United States Patent [19]

Byers

[11] Patent Number: 4,591,271

[45] Date of Patent: May 27, 1986

[54] METHOD AND APPARATUS FOR COATING DETECTION AND SURFACE EVALUATION

[76] Inventor: Donald W. Byers, 6955 SW. Sandburg Ave., Portland, Oreg. 97223

[21] Appl. No.: 477,330

[22] Filed: Mar. 21, 1983

[51] Int. Cl.$^4$ ............................................. G01N 21/00
[52] U.S. Cl. .................................... 356/432; 356/443; 356/445
[58] Field of Search ................. 356/38, 443, 445, 448, 356/382; 250/571

[56] References Cited

U.S. PATENT DOCUMENTS

| | | | |
|---|---|---|---|
| 2,359,873 | 10/1944 | Poindexter | 356/443 |
| 2,547,545 | 4/1951 | Strong | 356/443 |
| 3,353,025 | 11/1967 | Sturn. | |
| 3,559,555 | 2/1971 | Street. | |
| 3,577,885 | 5/1971 | Wells. | |
| 4,281,932 | 8/1981 | Young | 356/448 |
| 4,284,356 | 8/1981 | Heilman | 356/445 |

Primary Examiner—R. A. Rosenberger
Assistant Examiner—Crystal Cooper
Attorney, Agent, or Firm—Eugene D. Farley

[57] ABSTRACT

A primary beam of light is directed against the surface of a piece of material under conditions predetermined to generate a secondary beam by either transmission through the piece or reflection from the surface thereof. The secondary beam is directed against means for measuring the intensity of the transmitted or reflected light and the light intensity measured. The procedure is repeated on a different surface of the piece and the results compared. This gives an evaluation of the surface and a determination of the presence, absence, or condition of any coating which may be present on the surface. The apparatus of the invention comprises means for achieving the foregoing functions.

The method and apparatus are of particular application in the determination of which is the coated side of an object, such as a photographic film, or a coated lens.

7 Claims, 4 Drawing Figures

METHOD AND APPARATUS FOR COATING DETECTION AND SURFACE EVALUATION

BACKGROUND AND GENERAL STATEMENT OF THE INVENTION

This invention relates to method and apparatus for coating detection and surface evaluation. It pertains particularly to method and apparatus for detecting and evaluating coatings on pieces of material, which coatings because of their color or invisibility are difficult or impossible to detect and evaluate by visual observation.

In the photographic arts it is frequently necessary to identify the emulsion side of a photographic film or negative. For example, when making prints from photographic slides it is necessary to know which side of the slide is the emulsion side. If a mistake is made, and the slide is not oriented properly, during the duplicating operation, the picture will be reproduced backwards, i.e. the left side of the picture becomes the right side, and vice versa. If this occurs, the slide must be reprinted. This multiplies the operating cost because of requirements of individual handling, lost time in matching the reprint with the customer's order, scheduling disappointments and the like.

In the optical arts it also is necessary at times to determine quickly on which side of a coated base the coating occurs. This may be difficult, because to the human eye both sides appear the same. This is the case, for example, in the case of an optical grade beam splitter, or a mirror, wherein the glass has been surface coated.

Another instance in which it is desirable to verify the existence of a coating occurs in the metal processing arts, wherein metal surfaces are coated with various materials. For example, the surface of an opaque metal such as steel, aluminum, brass, etc. may be coated with a clear, transparent lacquer to produce a coating which is invisible to the unaided eye. The same situation exists when the metal base is coated with a material that is the same color as the metallic surface. This might occur when a silver or aluminum coating is applied to a silver or aluminum surface.

It is possible, of course, to solve the foregoing problem by scratching the surface to see if some of the coating material shaves off, or by applying a chemical to cause the coating to alter in some visible manner. Such procedures degrade or destroy the subject of the test, and are not usually commercially acceptable.

The need accordingly exists to provide method and apparatus for determining qualitatively on which side of a coated object the coating occurs. The need further exists to determine the condition of such a coating, i.e. whether it is a thick or a thin coating, or whether the coating is continuous or discontinuous.

It is the general purpose of the present invention to provide method and apparatus for achieving these ends.

Further objects of this invention are the provision of method and apparatus for determining the coating condition of a coated object which method and apparatus are qualitatively accurate; applicable to a wide variety of coated objects; applicable broadly to coated objects which may be either transparent, translucent or opaque; applicable to the detection of very thin coatings; simple, quick and easy to use; adaptable to automation; free from any tendency to damage either the coating or the substrate; and adaptable for use by unskilled operators.

I have discovered that the coated and uncoated surfaces of a wide variety of substrates have differing properties of transmission or reflectance of light. Accordingly, the foregoing and other objects of my invention may be accomplished by the provision of a method which broadly comprises directing a primary beam of light against the surface of the test piece, under conditions predetermined to generate a secondary beam of light. The secondary beam is either transmitted or reflected, depending upon whether the piece is transparent, translucent or opaque to the primary beam.

The secondary beam is directed against light intensity measuring means which measures the intensity of the secondary beam. The procedure is repeated on a different area of the test piece and the results compared. This determines not only the presence or absence of a coating, but also its quality i.e. whether it is a thick coating, a thin coating, a continuous coating or a discontinuous coating.

I have discovered further that the light transmissive and reflecting qualities of coated and uncoated surfaces may be intensified and made more readily observable by the expedient of applying to such surfaces a puff of condensible vapor. Many coated surfaces tend to absorb or diffuse the vapor. Other coated surfaces, under the same conditions of vapor application, tend to condense the vapor. The uncoated base surfaces have different capacities for vapor condensation to do the coated surfaces.

The resulting fogged surfaces have different qualities of light transmission and reflectance than the unfogged surfaces, to a very marked degree. This affords a positive and accurate tool for determining coating presence. It also provides a means of determining surface properties, since thick coatings and continuous coatings have greater capacity for dissipating the vapor, and vice versa.

DESCRIPTION OF SPECIFIC EMBODIMENTS OF THE INVENTION

In the following description, reference is made particularly to the application of the invention to the identification of the emulsion side and base side of photograph slides. No limitation thereby is intended, however, since the method may be applied to a wide variety of other articles, as described above.

Figure 1:
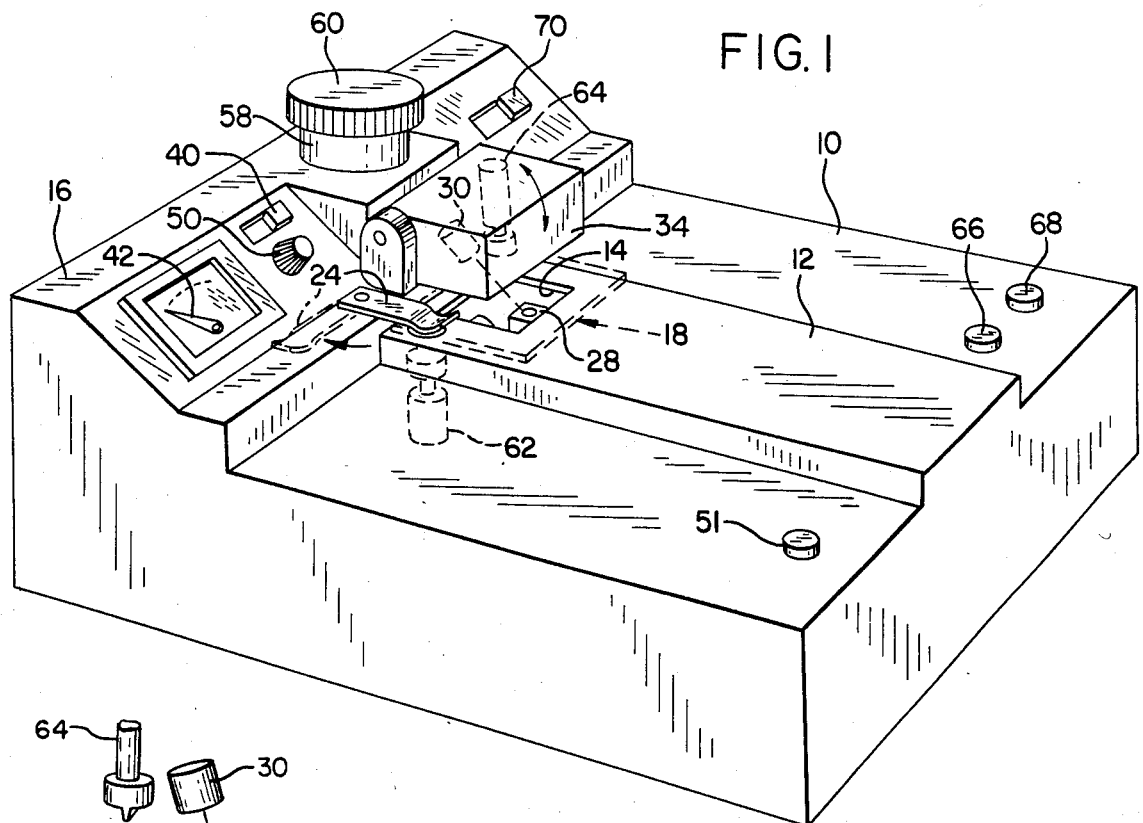
FIG. 1 is a view in top perspective of apparatus employed in coating detection and surface evaluation by the method of my invention.
Figure 2:
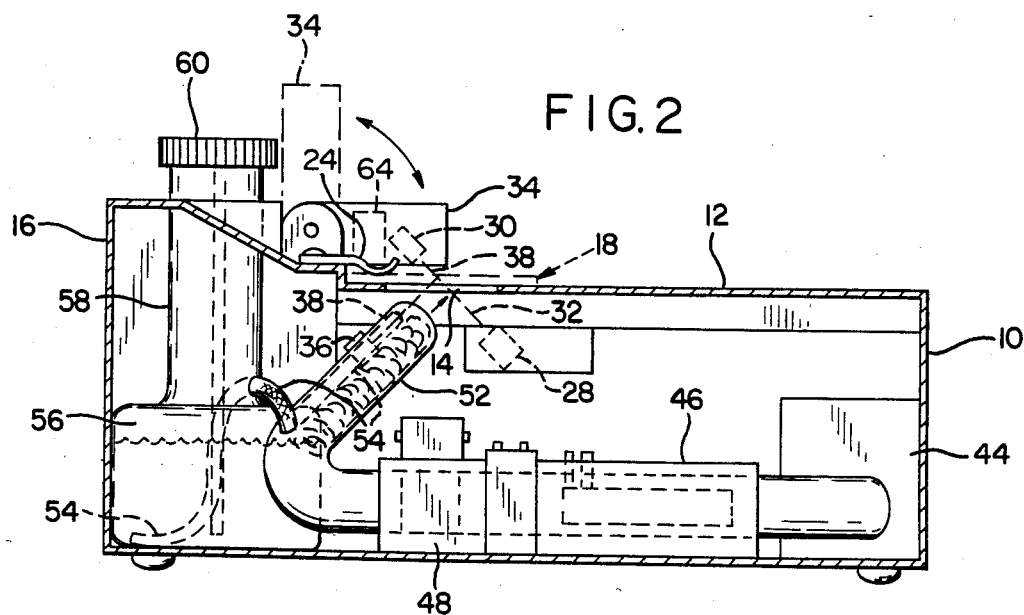
FIG. 2 is a longitudinal sectional view taken along lines 2—2 of FIG. 1.
Figure 4:
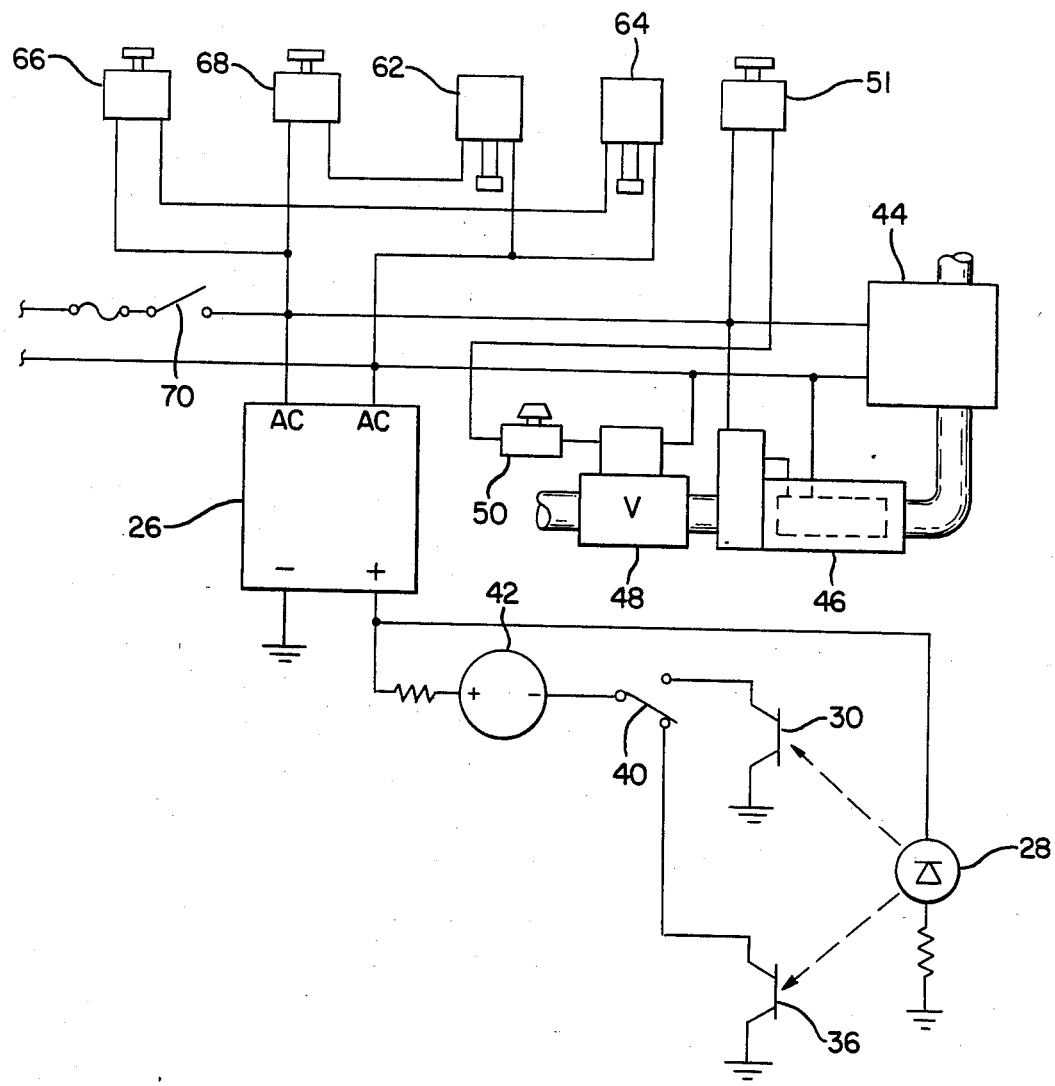
FIG. 4 is a circuit diagram of the apparatus of FIGS. 1 and 2.

Referring to FIGS. 1 and 2:

The apparatus is housed in a case 10 having on its upper surface a longitudinal bed 12. An aperture 14 is cut through the bed at its upper end. A console section 16 mounts the control instruments.

Means are provided for mounting a photographic slide over aperture 14.

As is conventional, the slide indicated generally at 18 (FIG. 3) comprises a film 20 mounted in a cardboard or plastic frame 22. A spring clip 24 releasably mounts the slide on the bed above aperture 14.

Means also are provided for directing a beam of light, preferably visible light, against the film, as it rests on bed 12 over aperture 14.

The illustrated light source comprises an electric circuit including a transformer 26 which supplies current of reduced voltage to a light-emitting diode 28. The latter is mounted beneath the aperture 14 in a position in which it will direct a beam of light 32 through the aperture at an appropriate angle, e.g. an angle of, preferably, from 30° to 60°.

Means also are provided for converting the light beam energy into electrical energy. In the illustrated form of the invention, such means comprise photoelectric cells, specifically photo transistors, 30, 36. Photo cell 30 is positioned for receiving a light beam 38 transmitted through the film, or other transparent or translucent object. It is preferably mounted in a hinged mount 34 which may be swung up out of the way in the event an opaque piece of material is to be tested.

A second photo cell 36 is mounted beneath the top of the case, in a position to receive a beam 38' (FIG. 3) of reflected light from light source 28, in the event that an opaque piece of material is being tested.

In this description, light beam 32 is characterized as being the primary beam, and beams 38 and 38' are characterized as being the secondary beams.

Also included in the electric circuit, together with light-emitting diode 28 and photo cells 30, 36 are a selector switch 40 and an ammeter 42. Selector switch 40 energizes one or the other of the photo cells, and ammeter 42 measures the current generated by the selected cell.

Also present in the presently described apparatus is a sub-assembly having for its function the generation of a puff of a condensible vapor to be applied to the surface of the article under inspection. As noted above, this has for its purpose the development of a film of condensed vapor on the test surface. If the subject matter of the test is a photographic slide and if the test surface is the base surface, a film of condensate will be formed. This film then will alter the light transmission or reflection qualities of the surface so that secondary beams 38, 38' will differ in intensity from primary beam 32.

If, on the other hand, the coated surface faces light source 28, the vapor condensate, if formed at all, is absorbed or dissipated so that a condensate film does not appear. In such a case, secondary beams 38, 38', whether transmitted or reflected, will have a much greater intensity.

As shown in FIG. 2, the vapor-generating and puffing subassembly comprises a source of air under pressure, which may be a connection to an air compressor, or, in the illustrated embodiment, a blower 44.

Blower 44 blows air continuously to a thermostat-controlled heater 46. The heater transmits heated air of controlled temperature through a solenoid-operated valve 48 and associated timer 50 to a discharge tube 52. Timer 50 is operated by switch 51 which controls the duration of the puff.

Discharge tube 52 is aimed or beamed at the underside of slide 18. It is packed with a wick 54 of porous, absorbent material.

Water or other liquid non degrading to the test piece and capable of serving as a source of condensible vapor is contained in a reservoir 56 fitted with a neck 58 and combination dip stick and cap 60. The dip stick measures the height of water in reservoir 56 so that it remains at a proper level and does not seep out the wick opening.

Marking means is provided for marking one side or the other of the test material, as required to indicate its coating condition. If it is desired to know which is the emulsion side of a photographic slide, for example, the test side may be marked with appropriate indicia.

The marking means employed for this purpose comprise a pair of solenoid operated stamps 62, 64, the former being for the underside of the slide and the latter for the upper side thereof. These are controlled at the will of the operator by means of switches 66, 68 respectively.

The entire circuit is energized by operation of an on-off switch 70.

OPERATION

The operation of the hereindescribed apparatus is as follows:

Where the piece comprises a photographic slide, the slide is mounted on bed 12 above aperture 14 in the manner indicated in FIGS. 1 and 2. It is retained by means of spring clip 24.

On-off switch 70 is closed. This energizes blower 44. Switch 51 is actuated. This energizes heater 46 which heats air supplied by the blower to the desired temperature.

Timer 50 is set to give the desired duration of puff by the discharge tube 52. Selector switch 40 is set in a position to energize photo cell 30.

When the air in the system has come to temperature, timer switch 50 is closed. This opens valve 48 for a time interval controlled by the time and predetermined to cause a puff of air of the desired duration to be emitted by discharge tube 52. As the warm air passes through the tube, it is saturated with moisture by means of wick 54, which is kept moist by water from reservoir 56.

As the puff impinges on the test surface of the slide, it condenses on the relatively cool surface, if the test surface is the base side. However, if it is the emulsion side, it does not condense appreciably because of the absorption or dissipation of the vapor by the substance of the emulsion coating.

The two sides then are distinguished by directing a beam of light from light-emitting diode 28 onto photo transistor 30. If the base side faces warm air discharge tube 52 and a film of water condensate is on the test surface, the light of the primary beam 32 will be dissipated with the result that the intensity of the secondary beam 38 will be diminished substantially. On the other hand, if the emulsion side of the film faces discharge tube 52, no, or little, condensation will be present, with the result that the intensity of primary beam 32 will not be diminished nearly as much, and the intensity of secondary beam 38 transmitted through the film will be correspondingly higher.

The operator can tell by glancing at ammeter 42 which is the case. If the ammeter reading is high, the emulsion side is down. If it is low, the base side is down. He then may mark the slide correspondingly by actuating one or the other of solenoid-operated stamps or markers 62, 64. This enables the duplicating machine operator to place the slide accurately in a duplicating machine.

Since the characteristics of condensation of moisture on the base side vs. non condensation on the emulsion side of all slides is similar, it is not necessary, when running a series of slides, to test both sides of each slide.

Both sides of the first slide may be tested and the comparative values of light transmission noted. Subsequent slides then may be tested on one side only. If the ammeter reading is high, the emulsion side is down, and vice versa. The appropriate side then may be marked with one of markers 62, 64, no matter which side is up.

It should be noted that in the case of many test pieces, the light transmission and reflection qualities of the base material and of the coating are such that the intensity of the secondary beam inherently will be different from that of the primary beam, depending upon whether the coating is in the face up or face down position. In such a case also, the application of the puff of condensible vapor to the test surface may be omitted.

As noted above, the apparatus of my invention is versatile in that it may be used to determine the coating condition of opaque objects, as well as of transparent or translucent objects. In the latter case, secondary beam 38 comprises transmitted light; in the former, secondary beam 38' comprises reflected light.

Figure 3:
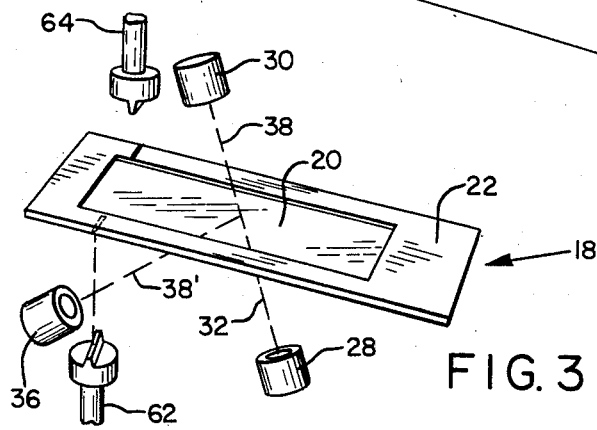
FIG. 3 is a top perspective detail view of a photographic slide illustrating the application of the method of my invention to determine which slide surface is coated with emulsion.

The manner in which the apparatus is adapted to the testing of opaque pieces is illustrated particularly in FIG. 3.

Photo transistor 30 is moved out of the way by hinging its mount outwardly to the dashed line position of FIG. 2. The position of spring clip 24 also is shifted. The opaque test piece then may be situated above aperture 14.

Selector switch 40 is set to energize photo transistor 36. The sequence described above for transparent materials then is followed, with or without the application of a puff of water vapor to the test surface, as circumstances dictate.

EXAMPLES

The following examples illustrate further the application of the hereindescribed apparatus.

A typical photographic slide was placed in the apparatus and both faces tested in the manner described above. The base side gave a reading of 0.25 milliamps. The emulsion side gave a reading of 0.63 milliamps, or a differential of about two and one-half times.

Accordingly, when subsequently testing a series of slides, if the tested surface gives a reading of about 0.25 milliamps it is the base side. If it gives a reading of about 0.63 milliamps it is the emulsion side. A qualitatively accurate scale of differential values may be established by the operator, and a positive means of accurately distinguishing between the two surfaces established.

Testing both surfaces of slides of various types and origin revealed that an ammeter reading of less than 0.4 milliamps indicates the base side, while an ammeter reading of over 0.4 milliamps indicates the emulsion side.

A group of test slides tested one at a time were rotated 360° and four readings taken on each side of every slide at 90° positions. In no case was a significant variation in reading obtained. This eliminates the possibility of a significant variation in test results being caused by the presence of a light or dark area on the slide picture.

The test procedure was applied to an optical beam splitter, or front coated mirror. Typical examples demonstrated a reading of 0.16 on the coated side and 0.33 milliamps on the uncoated side. In this case the coated side condensed more vapor than did the uncoated side.

A similar procedure was employed for testing an opaque test piece.

The test piece employed was an aluminum sheet spray-coated on one side only with a clear transparent acrylic coating. Visually the coated side appeared identical to the uncoated side. The apparatus was set with photocell 36 energized and photocell 30 deenergized. Testing in sequence the uncoated and coated sides of the piece, values of 0.45 milliamps were obtained for the uncoated side and 0.26 milliamps for the coated side.

The tests were repeated using a sheet of aluminum painted with silver enamel paint. In this case also both sides visually looked exactly the same. Even without the addition of vapor, the uncoated aluminum base gave a reading of 0.90 milliamps while the coated side gave a reading of 0.46 milliamps.

In a further test, a second coat of silver enamel paint was applied to the coated side of the aluminum sheet. In this case the reading on the doubly coated side was 0.19 milliamps. This compares with a value of 0.46 milliamps in the case in which the sheet had but a single coating. The apparatus thus was able to detect the presence of a double (thicker) coat of coating material.

The same test was carried out using an application of vapor to each side of the test piece. In this case the uncoated aluminum surface gave a reading of 0.45 milliamps, the surface sprayed with one coat of silver enamel gave a reading of 0.24 milliamps, and the surface sprayed with two coats of silver enamel gave a reading of 0.13 milliamps.

The versatility of my hereindisclosed method and apparatus thus is established. Using the apparatus, it is possible to determine positively the presence, thickness, and character of a wide variety of coating materials on substrates of various types, whether the substrate be transparent, translucent or opaque.

Having thus described my invention in preferred embodiment, I claim:

1. The method of determining the characteristics of a surface of a piece of material which comprises:
   (a) establishing the temperature of the piece at a temperature level below the condensation temperature of a selected condensable vapor,
   (b) impinging a puff of the vapor against said surface for a time duration sufficient to cause a predetermined condensation of the vapor thereon,
   (c) directing a primary beam of light against a surface of the piece under conditions predetermined to generate a secondary beam of light, the secondary beam being either transmitted or reflected, depending upon whether the piece is transparent, translucent or opaque to the primary beam,
   (d) receiving the secondary beam by light-measuring means,
   (e) measuring the intensity of the secondary beam,
   (f) repeating the foregoing sequence with reference to a second surface of the piece, and
   (g) by comparing the intensities of the two secondary beams determining the characteristics of the respective piece surfaces.

2. The method of claim 1 wherein the vapor comprises water vapor.

3. The method of claim 1 wherein the piece is a piece of photographic material comprising a base sheet having a photographic emulsion on one surface.

4. The method of claim 1 wherein the piece is a piece of photographic material comprising a base sheet having a photographic emulsion on one surface, and including the step of measuring the intensity of the secondary beam on both surfaces of the sheet, and thereafter comparing the relative intensities of the beams, thereby determining the coating condition of the piece surfaces.

5. Apparatus for determining the coating condition of a surface of a piece of material which comprises:
(a) a primary beam of light positioned for directing the beam against the surface of a piece under conditions predetermined to generate a secondary beam of light, the secondary beam being either transmitted or reflected depending upon whether the piece is transparent, translucent or opaque to the primary beam,
(b) light-intensity converting means positioned for receiving the secondary beam and converting it to an electric signal,
(c) electric signal measuring means connected to the converting means for measuring the intensity of the secondary beam, thereby determining the coating condition of the surface of the piece, and
(d) condensable vapor generating means positioned for impinging a puff of condensable vapor against the surface for a time duration sufficient to cause a predetermined condensation of the vapor thereon preliminary to directing the primary beam against the surface.

6. Apparatus for differentiating between the base side and the emulsion-coated side of transparent or translucent photographic film, which comprises:

(a) an electric circuit including light-generating means for generating a primary light beam,
(b) positioning means for positioning film in the path of the primary light beam, one side at a time, thereby generating a secondary light beam transmitted through the film,
(c) in the electric circuit, photoelectric cell means in the path of the secondary beam, and
(d) in the electric circuit, ammeter means for measuring the magnitude of the current generated by the photoelectric cell means, thereby measuring the intensity of the secondary beam for each side of the film and determining the coating conditions of the surface of the film against which the primary beam is directed,
(e) condensable vapor generating means, and
(f) means for impinging a puff of the vapor on the film surface preliminary to directing the primary beam thereagainst.

7. The apparatus of claim 6 wherein the vapor-generating means comprises a source of air under pressure, a thermostatically controlled heater for heating the air, a vapor discharge tube communicating with the heater and directed against the film surface, in the tube a wick saturated with water and valve means positioned for controlling the flow of air through the chamber as required to impinge a puff of vapor-saturated air against the film surface.

* * * * *